(12) United States Patent
Philimis

(10) Patent No.: US 11,771,341 B2
(45) Date of Patent: Oct. 3, 2023

(54) SYSTEM FOR DETERMINING FORCES AT THE FEET

(71) Applicant: CY.R.I.C Cyprus Research and Innovation Center Ltd, Nicosia (CY)

(72) Inventor: Panayiotis Philimis, Nicosia (CY)

(73) Assignee: CY.R.I.C. CYPRUS RESEARCH AND INNOVATION CENTER LTD, Nicosia (CY)

(*) Notice: Subject to any disclaimer, the term of this patent is extended or adjusted under 35 U.S.C. 154(b) by 609 days.

(21) Appl. No.: 16/636,179

(22) PCT Filed: Aug. 2, 2018

(86) PCT No.: PCT/EP2018/071073
§ 371 (c)(1),
(2) Date: Feb. 3, 2020

(87) PCT Pub. No.: WO2019/025572
PCT Pub. Date: Feb. 7, 2019

(65) Prior Publication Data
US 2020/0367788 A1    Nov. 26, 2020

(30) Foreign Application Priority Data

Aug. 3, 2017  (GB) .................................... 1712482

(51) Int. Cl.
*A61B 5/103*    (2006.01)
*A43B 17/00*    (2006.01)
(Continued)

(52) U.S. Cl.
CPC .............. *A61B 5/1038* (2013.01); *A43B 3/34* (2022.01); *A43B 17/00* (2013.01); *A61B 5/112* (2013.01); *A61B 5/1112* (2013.01); *A61B 5/6807* (2013.01)

(58) Field of Classification Search
CPC ... A61B 5/1038; A61B 5/1112; A61B 5/6807; A61B 5/112; A61B 5/1036;
(Continued)

(56) References Cited

U.S. PATENT DOCUMENTS 7,426,873 B1 * 9/2008 Kholwadwala .......... A43B 3/00
73/818
9,005,140 B2    4/2015 Mann et al.
(Continued)

FOREIGN PATENT DOCUMENTS

CN    101828794 A    9/2010
CN    105380342 A    3/2016
(Continued)

OTHER PUBLICATIONS

Intellectual Property Office of Singapore Search Report and Written Opinion published Jan. 8, 2021 (12 pages).
(Continued)

*Primary Examiner* — Patrick Fernandes
(74) *Attorney, Agent, or Firm* — Bejin Bieneman PLC

(57) ABSTRACT

The disclosure relates to a system for measuring forces at different regions of the foot for the purpose of supporting medical treatment, improving sports performance and so on. It uses a plurality of force sensors arranged in zones wherein the plurality force sensors include sensors of different types. The system includes a transmitter that transmits data to a processing unit that receives and processes data to determine performance of an athlete or medical conditions in relation to locomotion.

21 Claims, 14 Drawing Sheets

(51) Int. Cl.
  *A61B 5/11* (2006.01)
  *A61B 5/00* (2006.01)
  *A43B 3/34* (2022.01)

(58) Field of Classification Search
  CPC ... A61B 5/4866; A61B 5/1118; A61B 5/6829;
        A61B 5/2562; A61B 5/0024; A43B 3/34;
        A43B 17/00; A43B 3/00
  See application file for complete search history.

(56) References Cited

U.S. PATENT DOCUMENTS

| | | | | |
|---|---|---|---|---|
| 10,034,622 | B1* | 7/2018 | Mahmoud | A61B 5/1038 |
| 2006/0254369 | A1* | 11/2006 | Yoon | A61B 5/6804 |
| | | | | 73/862.041 |
| 2010/0063779 | A1* | 3/2010 | Schrock | G06F 3/0334 |
| | | | | 73/862.627 |
| 2010/0211355 | A1* | 8/2010 | Horst | A61B 5/1036 |
| | | | | 73/172 |
| 2011/0054359 | A1* | 3/2011 | Sazonov | A61B 5/1118 |
| | | | | 600/595 |
| 2011/0214501 | A1* | 9/2011 | Ross | A61B 5/6807 |
| | | | | 73/172 |
| 2013/0137943 | A1* | 5/2013 | Pinto Rodrigues | A61B 5/4866 |
| | | | | 600/595 |
| 2014/0222173 | A1 | 8/2014 | Giedwoyn et al. | |
| 2014/0326085 | A1* | 11/2014 | Lee | A61B 5/112 |
| | | | | 73/865.4 |
| 2016/0242646 | A1 | 8/2016 | Obma | |
| 2016/0299021 | A1 | 10/2016 | Thillainadarajah et al. | |

FOREIGN PATENT DOCUMENTS

| | | |
|---|---|---|
| EP | 0846441 B1 | 6/1998 |
| ES | 2120860 B1 | 11/1998 |
| KR | 20130080486 A | 7/2013 |
| KR | 101530225 B1 | 6/2015 |
| WO | 2006100331 A2 | 9/2006 |

OTHER PUBLICATIONS

International Search Report and Written Opinion for PCT/EP2018/071073 dated Mar. 15, 2019 (8 pages).

* cited by examiner

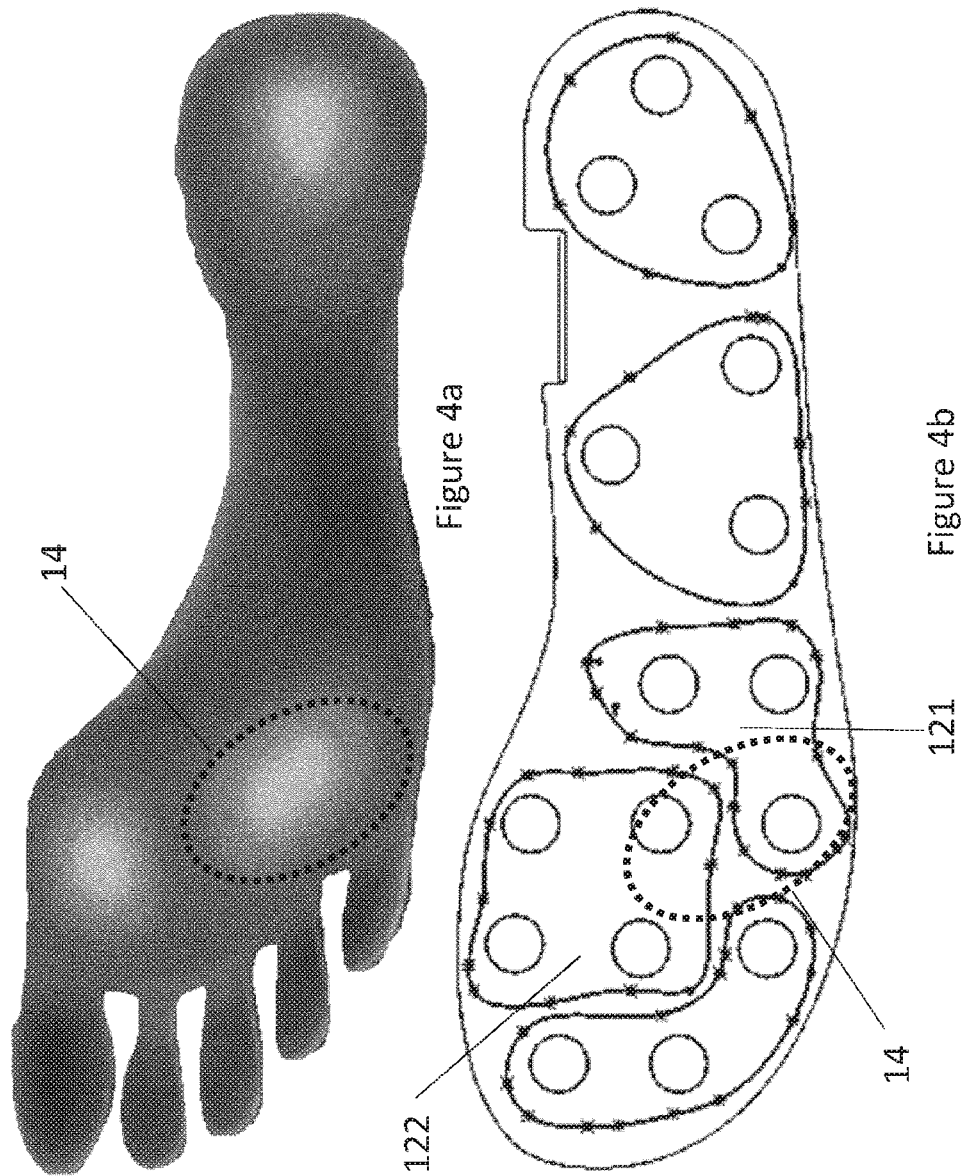

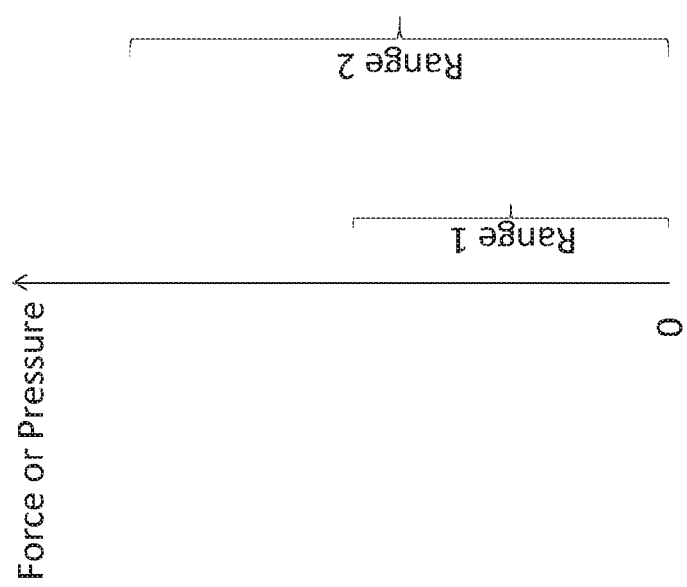

SYSTEM FOR DETERMINING FORCES AT THE FEET

CROSS-REFERENCE TO RELATED APPLICATIONS

This application is a national stage of, and claims priority to, Patent Cooperation Treaty Application No. PCT/EP2018/071073, filed on Aug. 2, 2018, which application claims priority to Great Britain Application No. GB1712482.7, filed on Aug. 3, 2017, which applications are hereby incorporated herein by reference in their entireties.

BACKGROUND TO THE INVENTION

Measurement of plantar pressure can be used for improving performance in sports and for diagnostic and rehabilitation or other purposes in healthcare. In-shoe force or pressure analysis can be used for medical purposes to help with rehabilitation, diagnose problems related to balance, sway, gait, or other foot functions. In-shoe force and pressure analysis can also be used to improve performance in sports, for example for track, football or basketball.

There are several solutions to the market that measure in-sole pressure and translate that into a visual pressure map or into force-time graphs. Force-time graphs can provide valuable information on physiology or performance. Frequently such data are used and assessed in comparison to a threshold or to an ideal profile, or to the user's historical data, in order to draw useful conclusions. For example, such conclusions may relate to proper positioning, strength, or synchronicity of an athlete.

Systems that are used for medical diagnostic purposes, can be considered as part of the investment in infrastructure that a clinic makes for example, and patients would just use these systems every time they visit their clinician. In other cases, for example in sports applications, users may have to each have their own pair of sensing shoes. For example, a football team may need to have more than 30 shoes for different players. For many applications therefore, low cost is an additional requirement to reliable data and fast response.

DESCRIPTION OF PRIOR ART

There are several known systems that use in-shoe pressure or force related measurements and which provide a profile of pressure distribution or force-time signals. The use of multiple sensors is well known in the art.

EP0846441 (B1) discloses sensors in arrays formed as a matrix addressable by rows and columns, each point in time interrogating the output of each row and column in a switchable manner. The problem with this arrangement is that a matrix of resistive type or strain type sensors is not very accurate and there is always a small time lag of the measurement of one physical point on the insole in relation to another physical point in the insole.

In a similar manner ES2120860 (B1) discloses a matrix arrangement consisting of 2048 piezoresistive elements. Although such approach makes it possible to find the pressure at any point of the footprint, there is a significant cost associated to this.

In many implementations, reliable pressure measurement requires a rigid layer upon which sensors rest. For example, U.S. Pat. No. 9,005,140B2 discloses an arrangement where the bottom layer of an insole is rigid. Such arrangement has the disadvantage that it is not suitable where good performance requires a flexible insole, as is the case with many sports related applications.

Most systems utilizing individual sensors, and process that data from each individual sensor. For example, US2014222173 (A1) discloses a system whereby a plurality of force sensors are used where there is at least one sensor in each of the phalange portion of the foot, a forefoot portion, and a heel portion. Each of the signals of the force sensors is compared to templates or other information related to that sensor. When individual pressure points are used, conclusions may be more difficult to draw as the system is critically dependent on the physiology of the user and each time needs to be recalibrated for the physiology of the user. Signal processing is also more complex the greater the number of sensors used, and failure of a single sensor may render the system useless.

Different special arrangements of sensors are known in the art and in many cases sensors are known to be organized in zones. For example, WO2006100331A2 discloses pressure surface that is divided into independent, adjacent zones and having numerous sensors. Each of the zones is equipped with an output terminal and a powered flexible printed circuit collects the terminals and conducts or transmits same wirelessly to an intelligent system which interprets the signals. The arrangement of sensors in zones is meaningful but the system can be very expensive if high accuracy sensors are used.

The objective of this disclosure is to provide an in-shoe sensing system that can be comfortably used for long periods and which can provide high reliability in measurements at a relatively low cost. The reliability of measurement should be safeguarded even if some sensor fails. A further objective of this disclosure is to allow comparisons among profiles of many users by enabling simplified signal processing that is not tied to the specific physiology of each individual user. This for example can be important for sports teams in trials or for a coach who needs to guide athletes or plan his game. Yet a further objective of this disclosure, is to enable a natural and comfortable feeling by being able to utilize an insole that can bend naturally.

SUMMARY OF THE DISCLOSURE

The disclosure includes a system for sensing in-sole force in a footwear including the use of a plurality of force sensors arranged in zones wherein the plurality force sensors include sensors of type A and sensors of type B. Type A and Type B sensors measure the same parameter, type A may be high range of force and type B may be low range of force. Alternatively, type A may be fast response rate, and type B slow response rate. Within each zone of the footwear, sensors are in contact with one or more rigid surfaces. The combination of type A and type B sensors arranged in zones enables good and reliable signals to be obtained without high cost. A flexible electronic circuit connects said force sensors, and a signal is transmitted to a processing unit.

BRIEF DESCRIPTION OF DRAWINGS

FIG. 1b illustrates an embodiment wherein the lower layer further includes depressions where sensors at least partially fit in.

FIGS. 4a and 4b illustrate an example of an alternative embodiment where rigid plates do not coincide with physiological pressure zones of the foot.

FIG. 6 illustrates and example of the different operating ranges of pressure or force sensors.

DETAILED DESCRIPTION OF THE DISCLOSURE

Figure 1A:
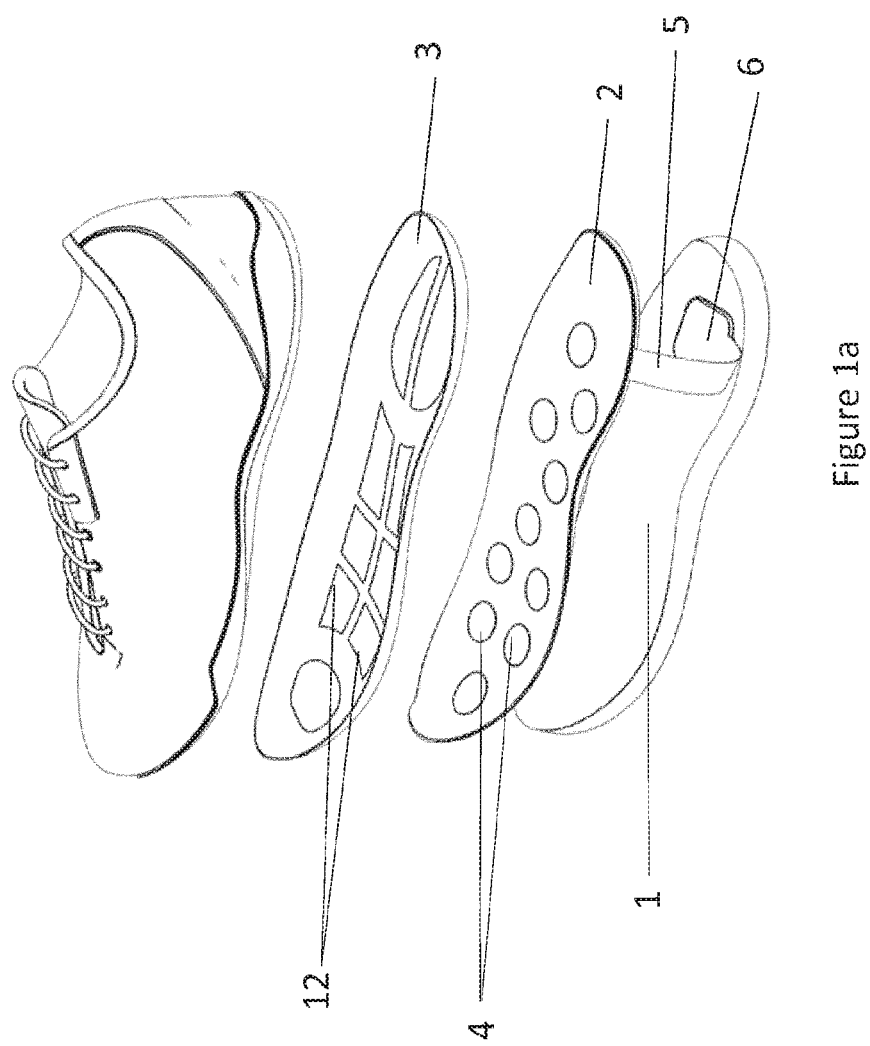
FIG. 1a illustrates an example of the layers of a sole of a shoe in a preferred embodiment wherein the system is integral to the sole of the shoe

With reference to FIG. 1a, the measuring system is integral with the sole (1) of the shoe and includes a lower layer (2), an upper layer (3), a plurality of sensors (4), a flexible electronic circuit (5) that connects said sensors (4), and a powering and handling unit (6). The lower layer is integral or in contact with the sole of the footwear and the upper layer is in contact with the foot, and the plurality of sensors include sensors of type A and Type B. Type A and Type B sensors measure the same parameter; type A may be high range of force and type B may be low force range. Alternatively, type A may be fast response rate, and type B slow response rate. The upper layer includes a number of rigid surfaces (12). The electronic circuit is connected to powering and handling unit (6) and to a processing unit. In a preferred embodiment, the processing unit is remote and data transmission is done wirelessly.

Figure 1B:
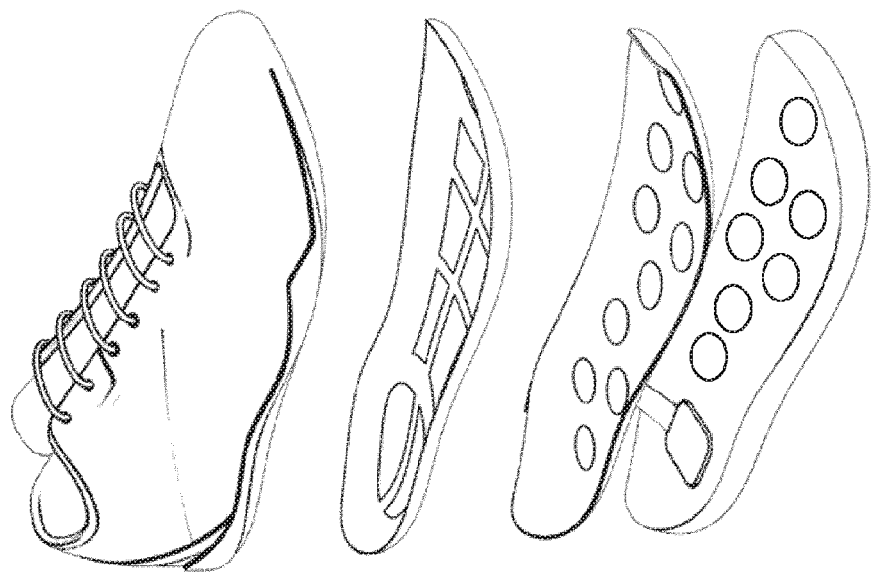

FIG. 1b shows an alternative embodiment wherein the lower layer (22) further includes depressions (16) where sensors (4) at least partially fit in.

In a preferred embodiment, sensors are force or pressure sensors. Force sensors may measure inferior-superior (vertical), anterior-posterior (back-front), and medial-lateral (side-to-side) forces experienced on the plantar surface of the foot. Inferior-superior or vertical ground reaction force is often the most significant force that is used to assess performance and medical condition.

The power supply (61) is in the form of a small battery, preferably a coin-type Li-Ion battery. The power supply may integrate a wireless charging capability (67) to recharge said battery. Memory (62) is preferably flash memory, e-PROM, e2-PROM, or other solid state memory. Transmission (64) is in a preferred embodiment a wireless transmitter, the form of which may vary depending of the application and the demands for transmission range. The power and handling unit may also integrate an integrated accelerometer and gyroscope component (65) to measure foot orientation, gait speed and acceleration. A GPS unit (66) may also be included in said power and handling unit to record geographic location of measurement and augment the accelerometer and gyroscope measurement to accurately position the footwear.

Figure 2:
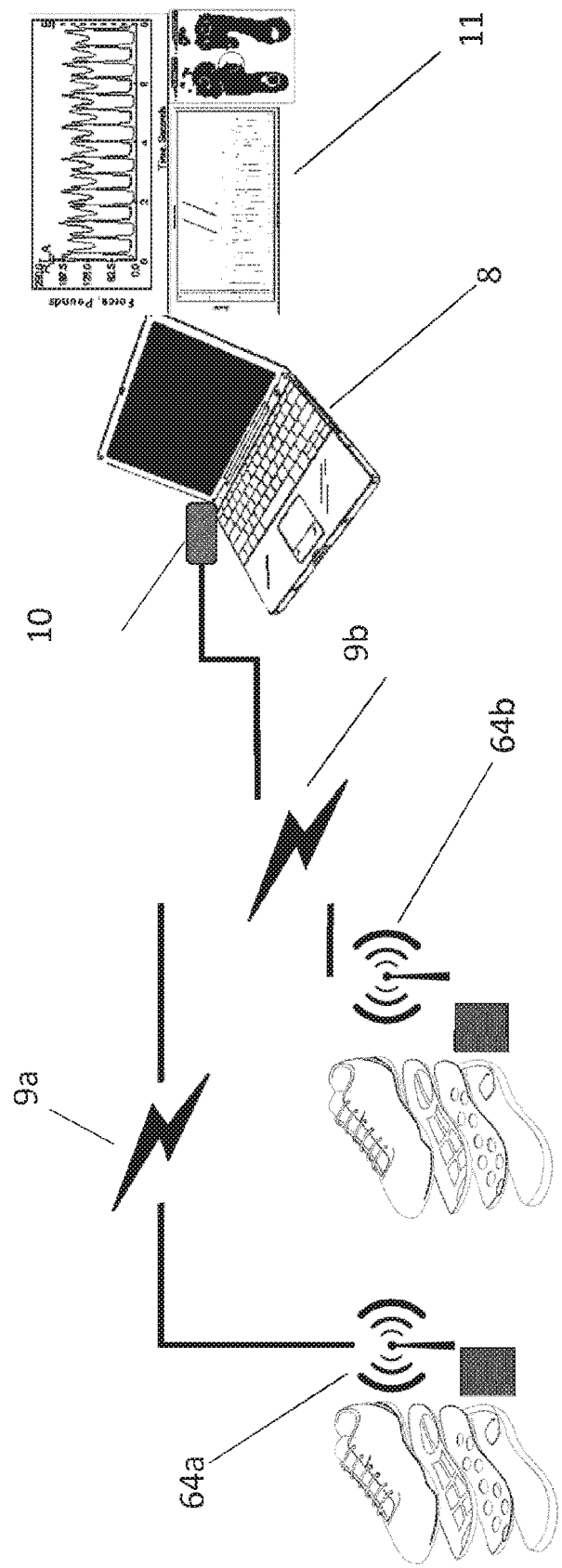
FIG. 2 illustrates an example of an overall system including devices in two shoes communicating with a processing unit

In a preferred embodiment, the processing of the data is done by a remote computer (8). FIG. 2 shows an embodiment where data is transmitted wirelessly, by transmission units (64a, 64b) in each shoe, to a remote computer (8). This remote computer may be for example a laptop or desktop computer, a smart phone or tablet, or another wearable or handheld device. Each measuring system at each shoe, generates a signal (9a, 9b) which is then transmitted to a computer receiver (10). The two signals (9a, 9b) are synchronized and then processed in order to provide visualizations (11) or other meaningful information after signal processing.

Triggering for recording can be done for example by a wireless signal that triggers both measurement systems at each shoe to start recording at the same time. Triggering may also be done when an internal clock at each measuring system in each shoe reaches a set time. The two clocks, one at each shoe, are synchronized in advance.

Data is collected as time series, and in one preferred embodiment processing includes comparisons of time series data. Such comparisons can for example indicate the degree of improvement that an athlete achieves over time.

Figure 3A:
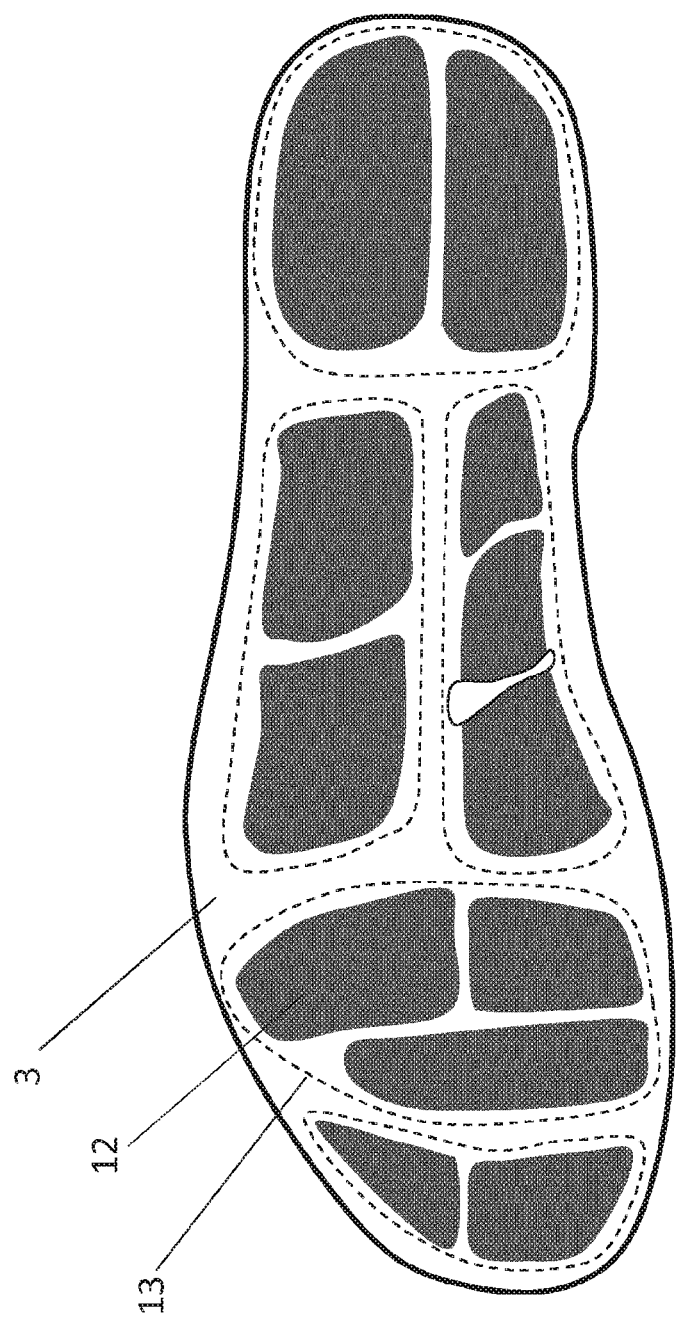
FIG. 3a illustrates an example of an embodiment with zones and rigid plates
Figure 3B:
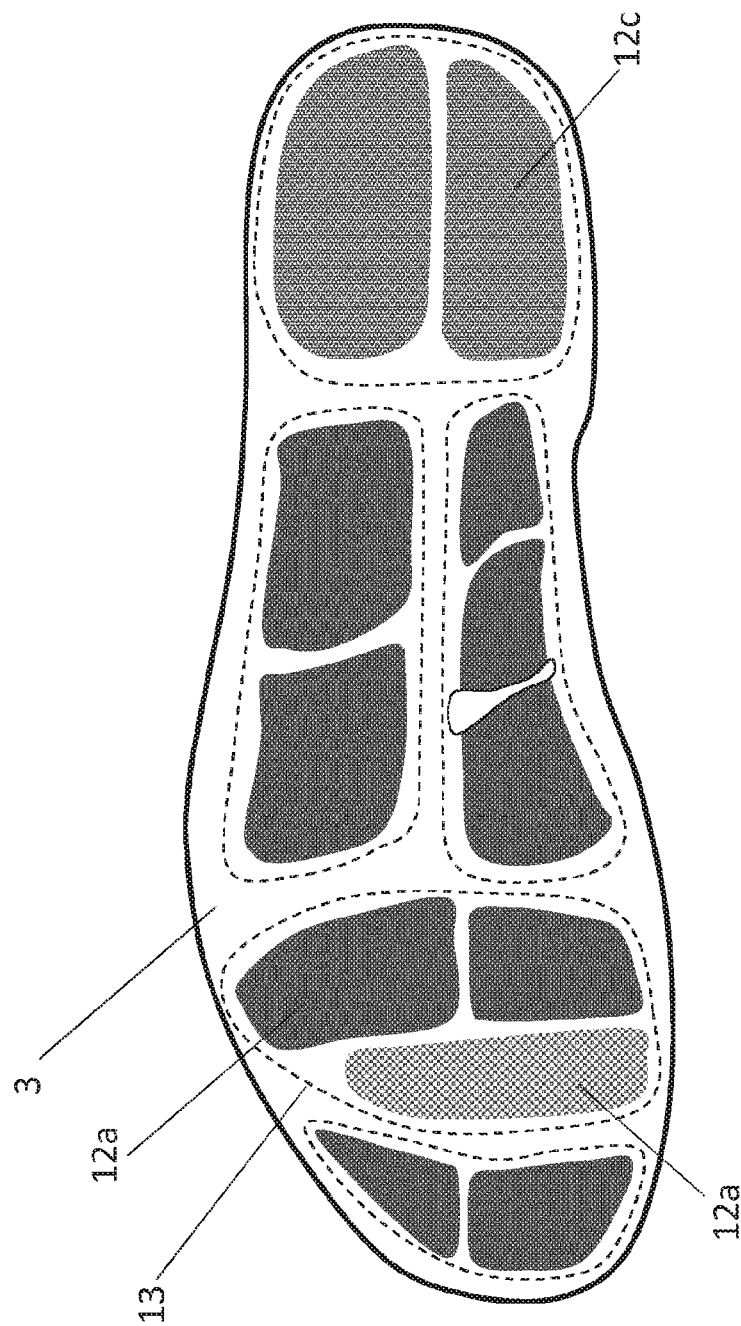
FIG. 3b illustrates an example of an embodiment with zones and rigid plates of different degree of rigidity

As illustrated by FIG. 3a, the upper layer (3, 31) that is in contact with the foot includes several rigid plates (12) which are organized in zones (13). These rigid plates are made of lightweight material such as carbon fibre composite. A certain degree of flexing is possible and in fact desirable for these rigid plates (6). Different rigid plates (12) may have a different rigidity or a different degree of flexing depending on the position or the application. FIG. 3b shows an example of layer including rigid plates of different rigidity (12a, 12b, 12c). Rigidity is necessary to ensure that force is effectively transferred to the different sensors (4) that are in contact with a rigid plate (12). A balance of high, medium, or low rigidity provides comfort and natural movement while satisfying the objective of transferring force or pressure to the sensors.

Rigid plates may not always match the pressure regions of the food applied to the shoe. FIG. 4a shows a typical pressure region (14) of a foot and FIG. 4b shows the same region (14) matched onto the upper layer of a measuring system. In this example, the pressure region spans two rigid plates (121,122).

Figure 5A:
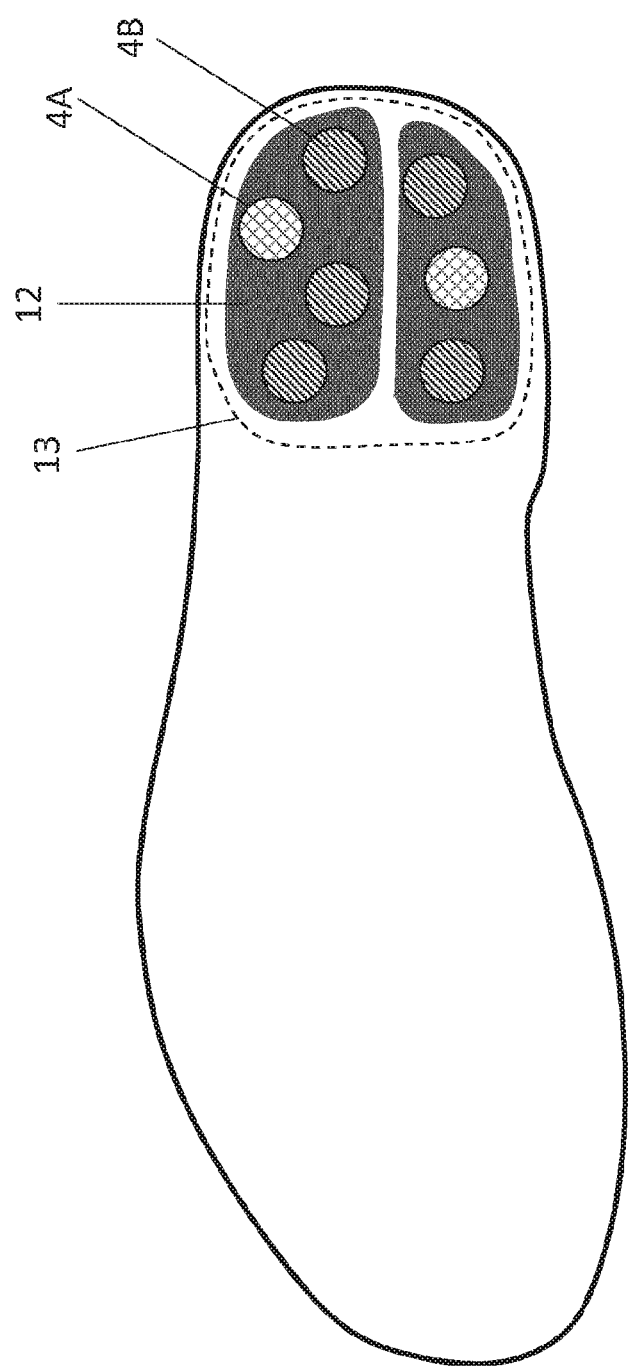
FIG. 5a illustrates an example of an embodiment with sensors positioned at the heel zone showing type A and type B sensors.

A single rigid plate generally is in contact both with sensor Type A (4A) and sensor Type B (4B). FIG. 5a illustrates an arrangement in one preferred embodiment where each of the shown rigid plates (12) is in contact with two types of sensors, both Type A (4A) and Type B (4B). By having both type A and type B sensors in contact with the same rigid plate, the signal can be effectively averaged out, while fluctuations are higher frequencies can be captured by the sensor with the faster response rate.

Figure 5B:
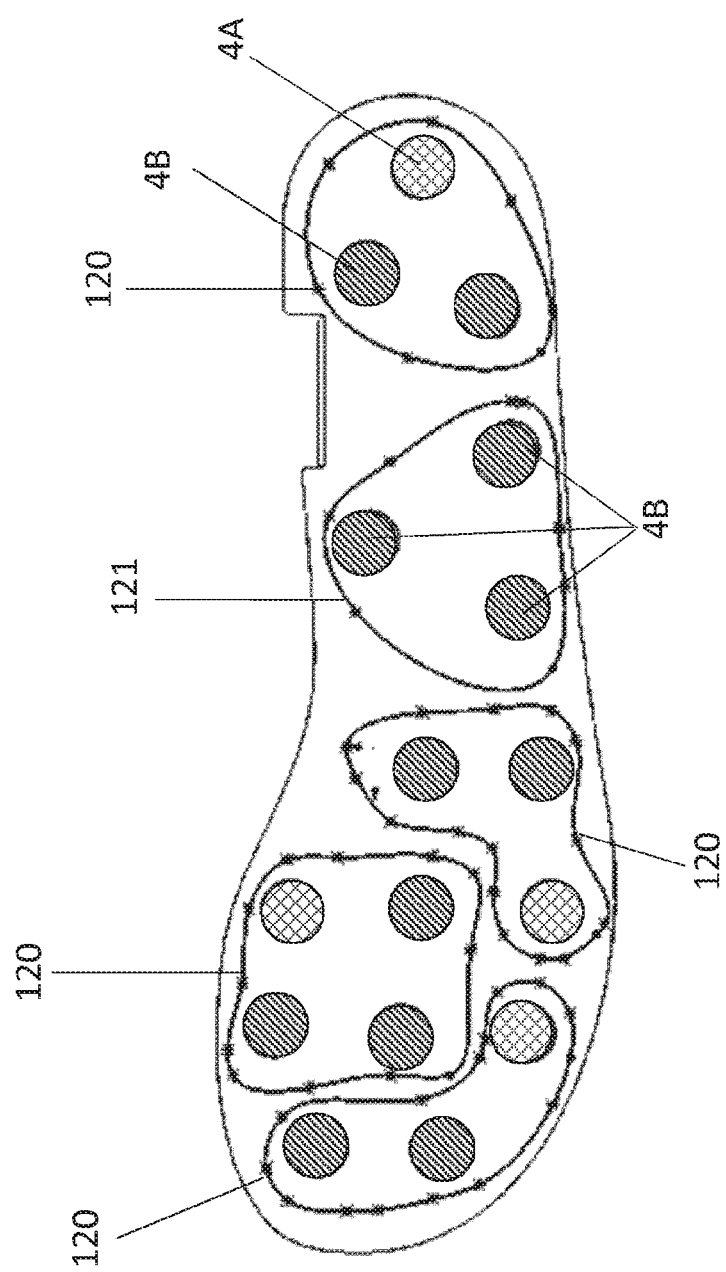
FIG. 5b illustrates an example of an embodiment with sensors Type A and Type B arranged at different zones.

A single rigid plate may not be in contact with both sensor type A (4A) and sensor type B (4B). FIG. 5b shows an arrangement in an alternative embodiment where a zone (121) is in contact with sensors of one type only, type B (4B), whereas other zones (120) are in contact with both sensor type A and sensor type B. For example, sensor type B may represent a sensor of slower response rate, and hence being of a lower cost.

The arrangement whereby a zone includes both type A and type B sensors, where type A may be a sensor covering one pressure range and type B may be a sensor covering another pressure range, enables high overall accuracy and reliability at much lower cost. FIG. 6 shows an example of force or pressure ranges that sensors may cover. Generally, sensors that maintain high accuracy over a long range tend to be more expensive than sensors that maintain accuracy over a smaller range. Type A and Type B sensors may represent sensors operating at a different range of force or pressure measurement. In this way, higher resolution is achieved for a lower cost by combining the signals from two sensors each operating at a narrow range, since sensors operating at a wider range are generally more expensive than sensors operating at a narrow range for the same resolution.

Typically errors in sensors are less in the region of 10-50% of full scale. For example, a sensor that measures zero to 100 Kg, when measuring 5 Kg force would have a much greater error than a sensor that has an operating range zero to 50 Kg force and measures 5 Kg force.

Different types of sensors may include different sensing specifications, for example different operating ranges, different sensing area, different full scale (FS) accuracy and different linearity, drift and repeatability. The lower the cost of a sensor generally the lower the accuracy, linearity or repeatability.

The use of different types of sensors also allows for the use of a higher performance sensor, such as higher accuracy sensor, to be used to calibrate a lower performance sensor thus achieving good performance at much lower cost.

In a configuration where several sensors (4) are in contact with a rigid plate (12) signal processing can be simplified by taking a value of the average of the values from each individual sensor for those sensors for whom the actual force value is within their operating range. By using simple averages comparisons and visual examination of force or force maps is made a lot easier for the medical doctor or for a sports coach for example.

In a configuration where several sensors (4) are in contact with rigid plates (12) it is also possible to compensate for failure of a single sensor enabling the system to continue to be used even if one sensor fails.

In a configuration where several sensors (4) are in contact with rigid plates (12) in zones (13), by taking the sum of individual sensor values in each zone, the total force value for that zone is calculated. Force values for each zone are summed to provide the total vertical ground reaction force value for said footwear.

Figure 7:
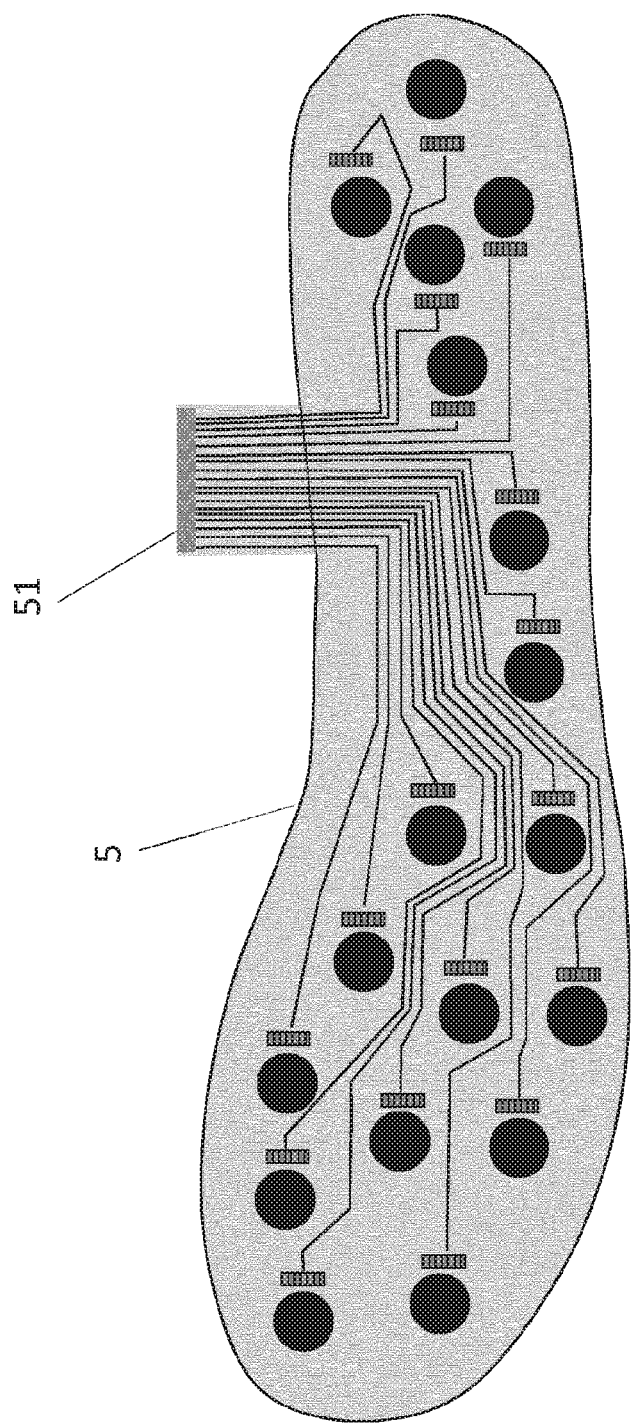
FIG. 7 schematically illustrates and example of sensors mounted onto flexible electronic layer.

Sensors are connected to a flexible electronic circuit which is in turn connected to the powering and handing unit (6). FIG. 7 shows an example of such flexible electronic circuit. It is possible that all components on such circuit are printed and flexible. A flexible connector (51) leads to the powering and handing unit (6). Several sensors (4) connected to the flexible electronic circuit (5). In another embodiment, sensors are integral to the flexible electronic circuit, and are produced by direct printing techniques.

Figure 8A:
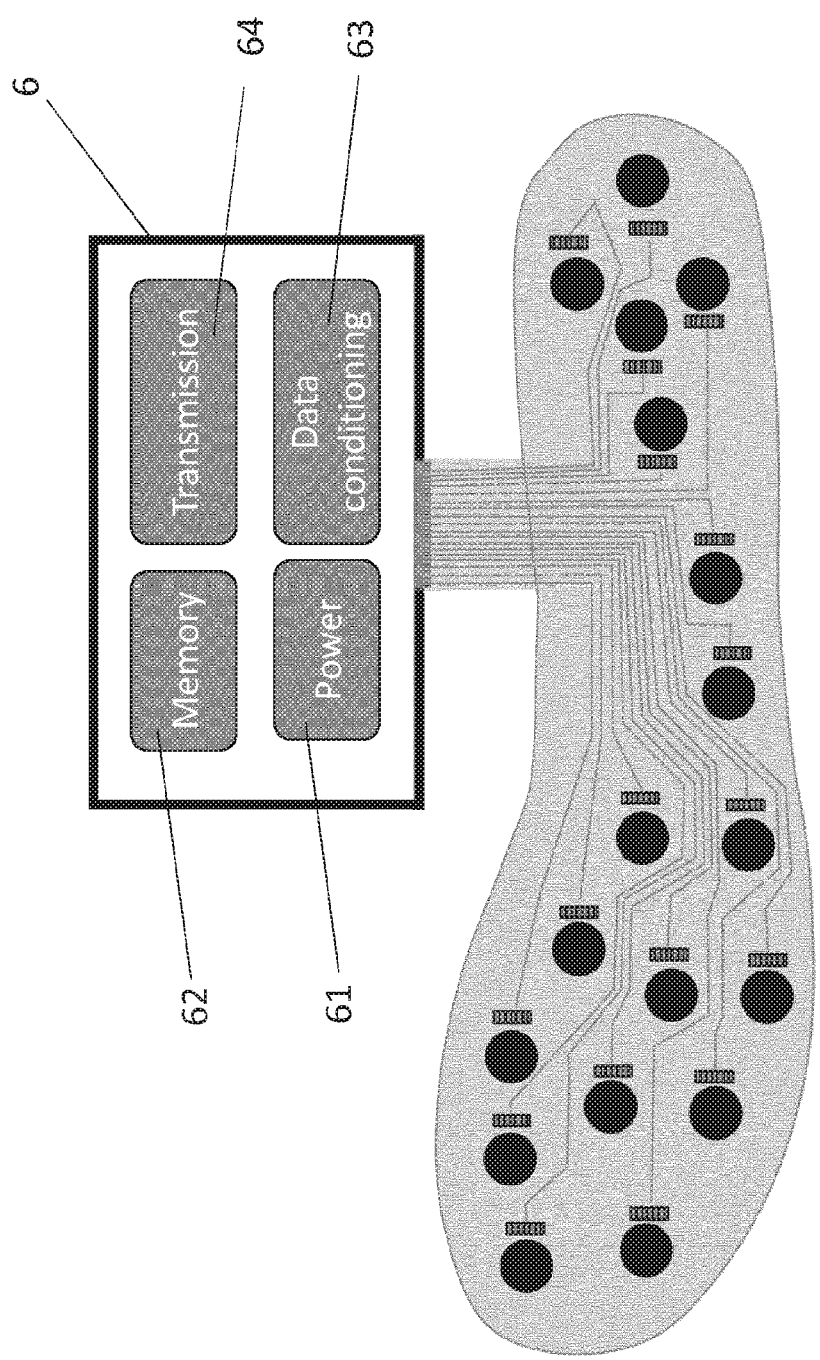
FIG. 8a schematically illustrates the modules of the power and handling unit.

FIG. 8a shows the powering and handing unit (6) which includes power supply (61), memory (62), data conditioning (63), and transmission (64). The power supply (61) is in the form of a small battery, preferably a coin-type Li-Ion battery. Memory (62) is preferably flash memory, e-PROM, e2-PROM, or other solid-state memory. It is also possible that there is no memory, and data is transmitted directly as generated. Transmission (64) is, in a preferred embodiment, a wireless transmitter. The specific transmitted technology depends on the application and the demands for transmission range. In another embodiment, there is no data transmission. Data is stored in memory and downloaded when the shoe is in proximity to a computer by connecting a communication device to a connection port that accesses memory. Such port could be for example a USB port.

Figure 8B:
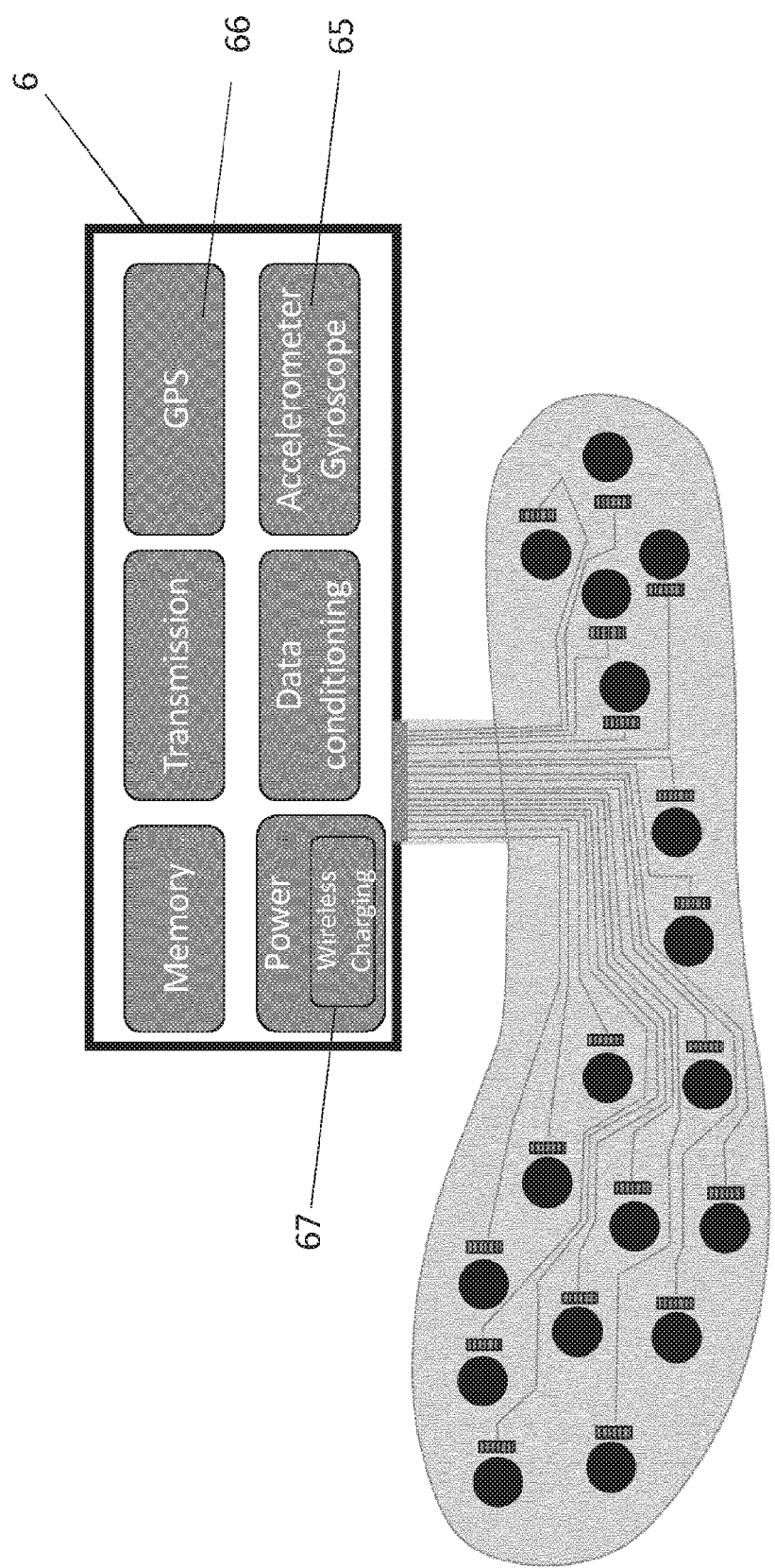
FIG. 8b schematically illustrates the modules of the power and handling unit with embedded accelerometer, gyroscope and wireless charging capability.

FIG. 8b shows the power and handling unit with embedded accelerometer and gyroscope (65), GPS (66) and wireless charging capability (67). An integrated accelerometer and gyroscope component (65) is used to measure foot orientation, gait speed and acceleration. A GPS unit (66) is used to record geographic location of measurement and augment the accelerometer and gyroscope measurement to accurately position the footwear.

Figure 9B:
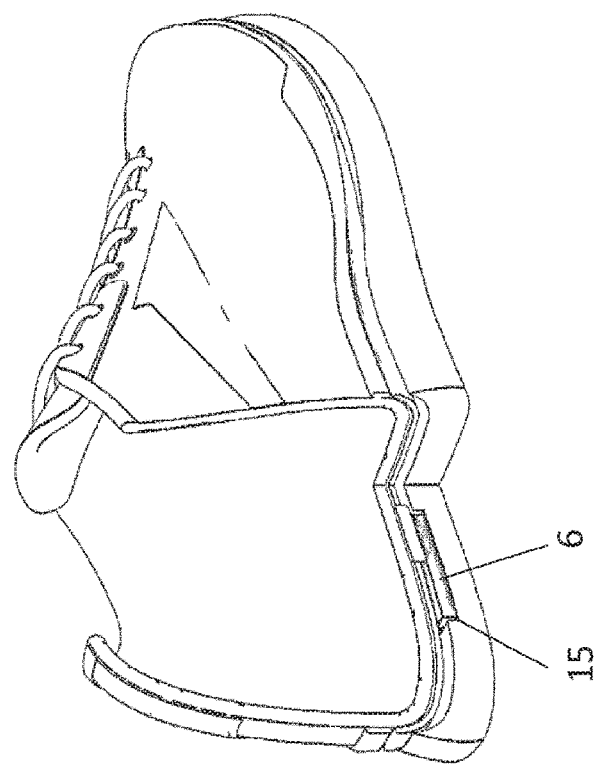
FIGS. 9a and 9b illustrate the positioning of the power and handling unit into a depression in the sole of the shoe.
Figure 9A:
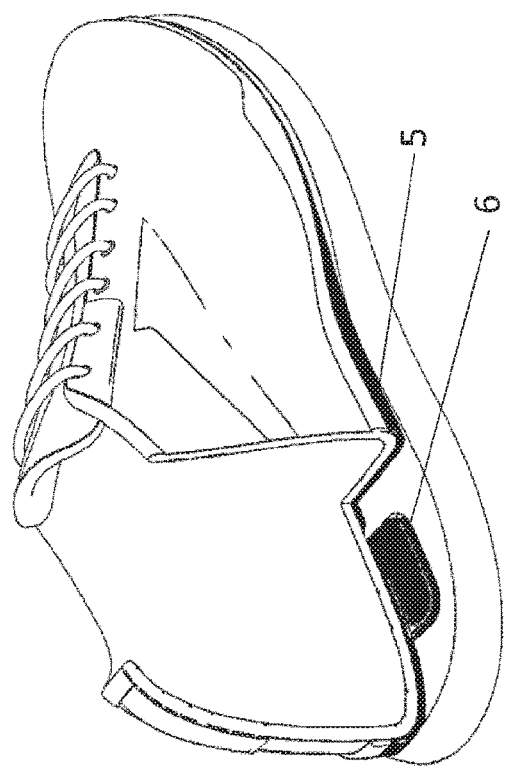

FIGS. 9a and 9b illustrate a preferred embodiment where the powering and handing unit (6) is secured in a cavity (15) within the sole of the shoe. This has the advantage that the powering and handing unit is completely concealed. On the other hand, this may have negative impact regarding the performance of the shoes such as rebound and shock absorption and may also have a negative impact on the range of the transmitted.

Figure 10:
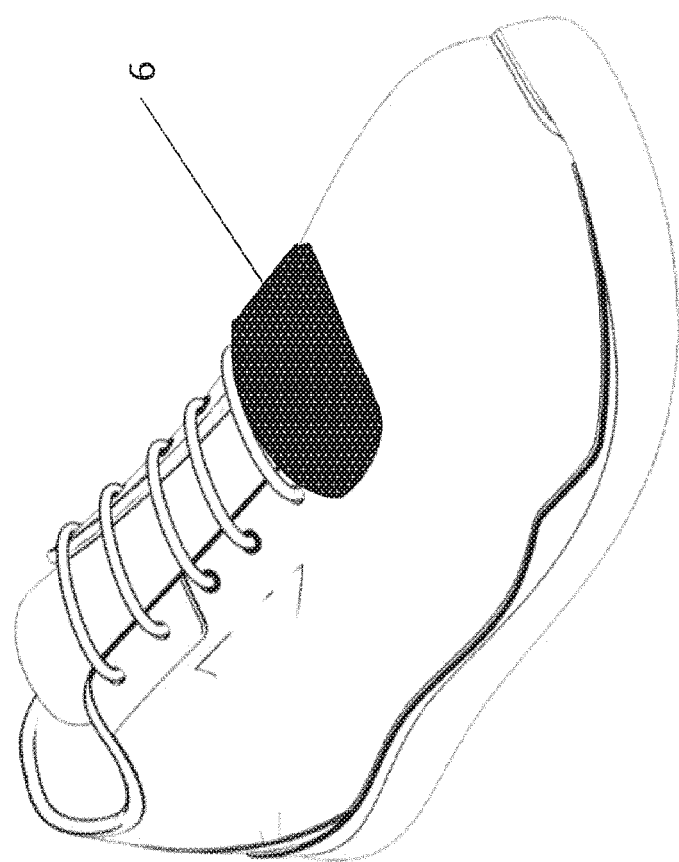
FIG. 10 illustrates an alternative positioning of the power and handling unit at a position outside the sole of the shoe.

FIG. 10 shows an alternative embodiment wherein the power and handing unit may be secure on the external upper surface of the shoe, and the flexible electronic circuit may be in I communication with the powering and handing unit (6) via a long flexible connector (51).

In this description and in the claims of this disclosure pressure and force may be used interchangeably as both parameters fundamentally relate to the same physical condition of the foot and pressure is force distributed on the area of a sensor.

The invention claimed is:

1. A system for sensing in-sole force in a footwear, the system comprising:
a lower layer, an upper layer, a plurality of force sensors arranged in a plurality of zones, a flexible electronic circuit that connects said plurality of force sensors, and a power and handling unit connected to the electronic circuit, said power and handling unit receiving raw signals from said plurality of force sensors wherein the lower layer is integral or in contact with the sole of the footwear and the upper layer is configured to be in contact with a foot;
said plurality of force sensors include at least two different types of force sensor, type A and type B, wherein type A and type B force sensors differ in the following way: type A has a higher range of force than type B, type A has a greater accuracy than type B, or type A has a faster response rate than type B.

2. A system according to claim 1, wherein the upper layer includes one or more regions of rigid material and regions of flexible material.

3. A system according to claim 2, wherein each region of rigid material is placed above at least part of each zone of the plurality of zones.

4. A system according to claim 2, wherein each zone of the plurality of zones is in contact with the one or more regions of rigid material of the upper layer.

5. A system according to claim 1, wherein force measurements from each of the plurality of force sensors in each of the plurality of zones are summed or averaged to provide a total or average force value for that zone.

6. A system according to claim 5, wherein signals used for calculating forces include signals from the plurality of force sensors wherein a read value falls within a defined minimum and maximum value of an operating range of the plurality of force sensors.

7. The system according to claim 1, wherein the plurality of force sensors includes forces sensors of one force range and force sensors of another, different force range and the force sensors of the one force range are used to calibrate the force sensors of the another, different, force range.

8. A system according to claim 1, wherein zones of the plurality of zones at a front region of the foot include at least one force sensor with a wide measuring range, covering all values that the zones at the front region of the foot may encounter.

9. A system according to claim 1, wherein force sensors of the plurality of force sensors measure force in vertical or traverse or longitudinal direction.

10. A system according to claim 1, wherein force sensors of the plurality of force sensors measure vertical ground reaction force.

11. A system according to claim 1, wherein the flexible electronic circuit includes a wireless transmitter and a processing unit is connected to the flexible electronic circuit wirelessly.

12. A system according to claim 1, wherein a processing unit is configured to be worn by a user.

13. A system according to claim 12, wherein said processing unit is a smart phone or another wearable device, wherein a dedicated application is processing force sensor data.

14. A system according to claim 1, wherein the flexible electronic circuit and the plurality of force sensors are integrally connected and form an intermediate layer between said upper layer and said lower layer.

15. A system according to claim 1, wherein the flexible electronic circuit includes a memory module wherein data may be downloaded from the memory module to an external processing unit.

16. A system according to claim 1, wherein the lower layer includes depressions where force sensors of the plurality of force sensors at least partially fit in.

17. A system according to claim 1, wherein the lower layer includes regions of different rigidity.

18. A system according to claim 1, wherein data is collected as time series, and wherein processing includes comparisons of time series data.

19. A system according to claim 1, wherein an accelerometer and gyroscope are included in said power and handling unit to measure foot orientation, gait speed, and acceleration.

20. A system according to claim 1, wherein a GPS is included in said power and handling unit to record location.

21. A system according to claim 1, wherein power is provided by a rechargeable battery, a processing unit integrating a wireless charging capability to recharge said rechargeable battery.

* * * * *